United States Patent [19]
Calderon-Garciduenas

[11] Patent Number: 5,672,151
[45] Date of Patent: Sep. 30, 1997

[54] INTRAPALMAR ORTHOSIS

[76] Inventor: Jose Calderon-Garciduenas, Paris #17 Col. Mirador 64070, Monterrey, Nuevo Leon, Mexico

[21] Appl. No.: 785,155

[22] Filed: Jan. 13, 1997

Related U.S. Application Data

[63] Continuation of Ser. No. 572,012, Dec. 14, 1995, abandoned.

[51] Int. Cl.$^6$ .................................................. A61F 5/00
[52] U.S. Cl. .................................. 602/21; 602/20; 602/64
[58] Field of Search .............................. 602/20, 21, 22, 602/60, 61, 62, 64; 128/869, 878, 879, 880; 2/455, 16, 159, 161.1, 161.6, 161.7

[56] References Cited

U.S. PATENT DOCUMENTS

| | | | |
|---|---|---|---|
| 5,350,418 | 9/1994 | Janevski et al. | 602/21 |
| 5,397,296 | 3/1995 | Sydor et al. | 602/21 |
| 5,413,553 | 5/1995 | Downes | 602/21 |

*Primary Examiner*—Richard J. Apley
*Assistant Examiner*—Kim M. Lee
*Attorney, Agent, or Firm*—Laurence R. Brown

[57] ABSTRACT

Intrapalmar orthosis to protect and give stability to the carpus' zone of the hand, without limiting normal the hand's movement, which consists of one semiflexible or rigid support splint arranged on a gauntlet to put on the hand' palm, the splint forming a whole body. Once incorporated to the hand, the splint functions only if the hand is working, then a firm pressure is exerted over the palmar face of the carpus.

4 Claims, 5 Drawing Sheets

INTRAPALMAR ORTHOSIS

This application is a continuation of application Ser. No. 08/572,012, filed Dec. 14, 1995, now abandoned.

FIELD OF THE INVENTION

This invention relates to an intrapalmar orthosis to protect and give stability to the carpus' palmar zone of the hand, giving support to the carpus.

DESCRIPTION OF THE PRIOR ART

For many years in medical practice of prevention and rehabilitation, several orthoses have been implemented, with the purpose of protecting wrist and hand, having as a common characteristic that they cross the wrist and have a rigid structure, which limits the wrist's and finger's free movement; other splints are elastic, offering no support to the osseous structures of the carpus, other are designed with gel or similar materials, neither giving any support to the osseous carpus, but serving to absorb vibrations when working with pneumatic tools or the like, numbing one's function because of their size and distribution, all of them offer no specific support to the carpus' palmar zone.

For the first time as far known, with the use of this invention, it will be possible to make hand's movements easily and comfortably, because its support is limited to the carpus palmar zone.

The intrapalmar orthosis has a significant advantage, because its use is comfortable and it doesn't interfere with the hand's function, so someone may use it all time if it be necessary, or during normal activities, including work time.

This invention is of generic use, specially for protecting the carpus' palmar region and giving support to the carpus in case of instability.

SUMMARY OF THE INVENTION

Intrapalmar hand's orthosis for palmar support of the carpus, designed to be used by workers who manually manage materials and by patients with carpus problems.

Intrapalmar orthosis comprehends a semiflexible or rigid plate of polyproylene, polyethylene or similar plastic material to be placed on the hand's carpus palmar region and a fastening gauntlet to be incorporated to the hand, closing in the hand's dorsal region; the orthoses semiflexible support is included in the gauntlet.

One object of this invention is to provide a firm palmar support to the carpus bones during manual work and when there is a carpus instability or pain, allowing free movement of hand and wrist. Another object is to provide its use in moderate and heavy manual activities without interfering with the hand's function, without causing a loss of labor efficiency.

DESCRIPTION OF THE INVENTION

Figure 4:
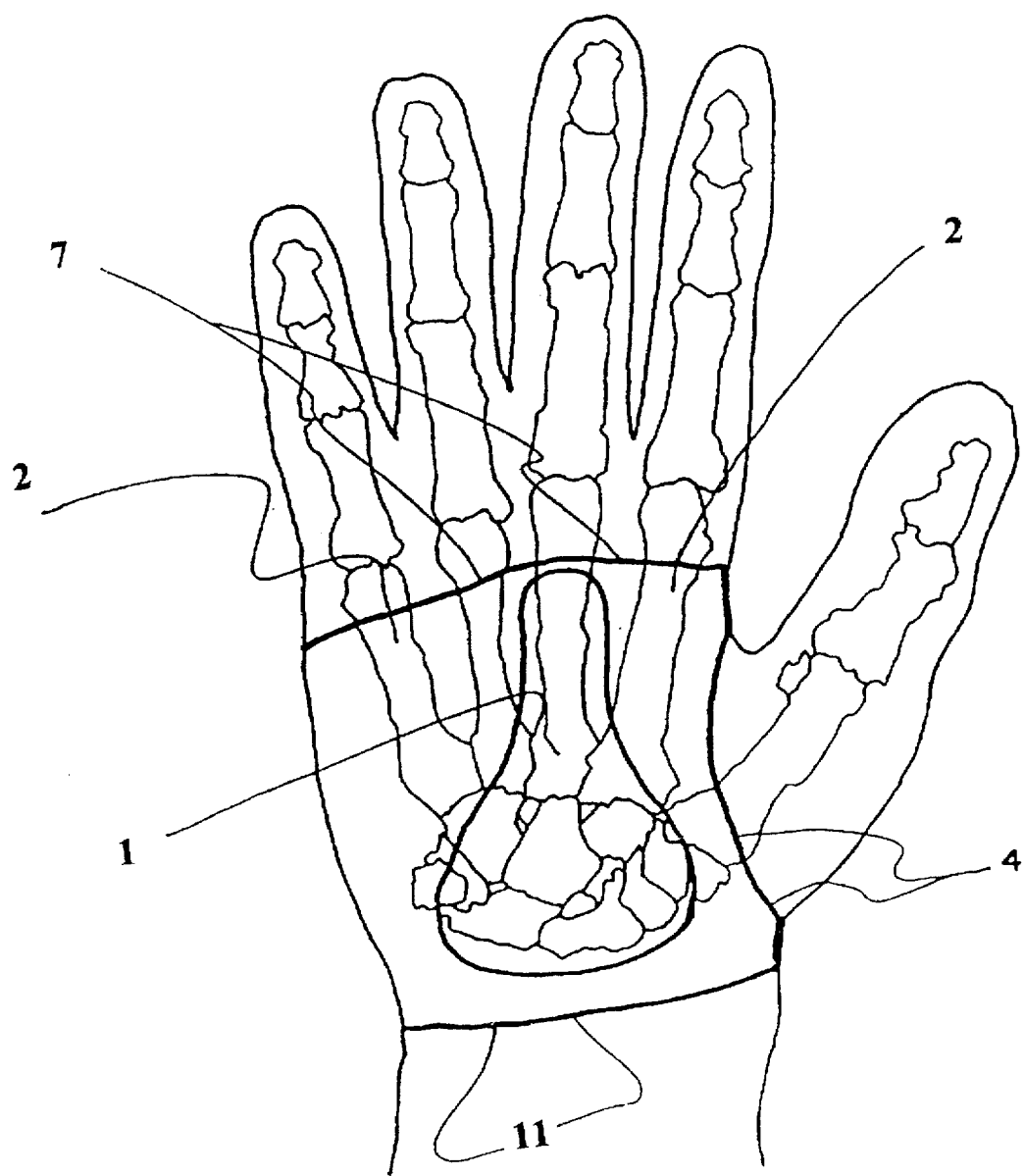
FIG. 4 is a frontal view of the orthosis, worn on the hand.
Figure 5:
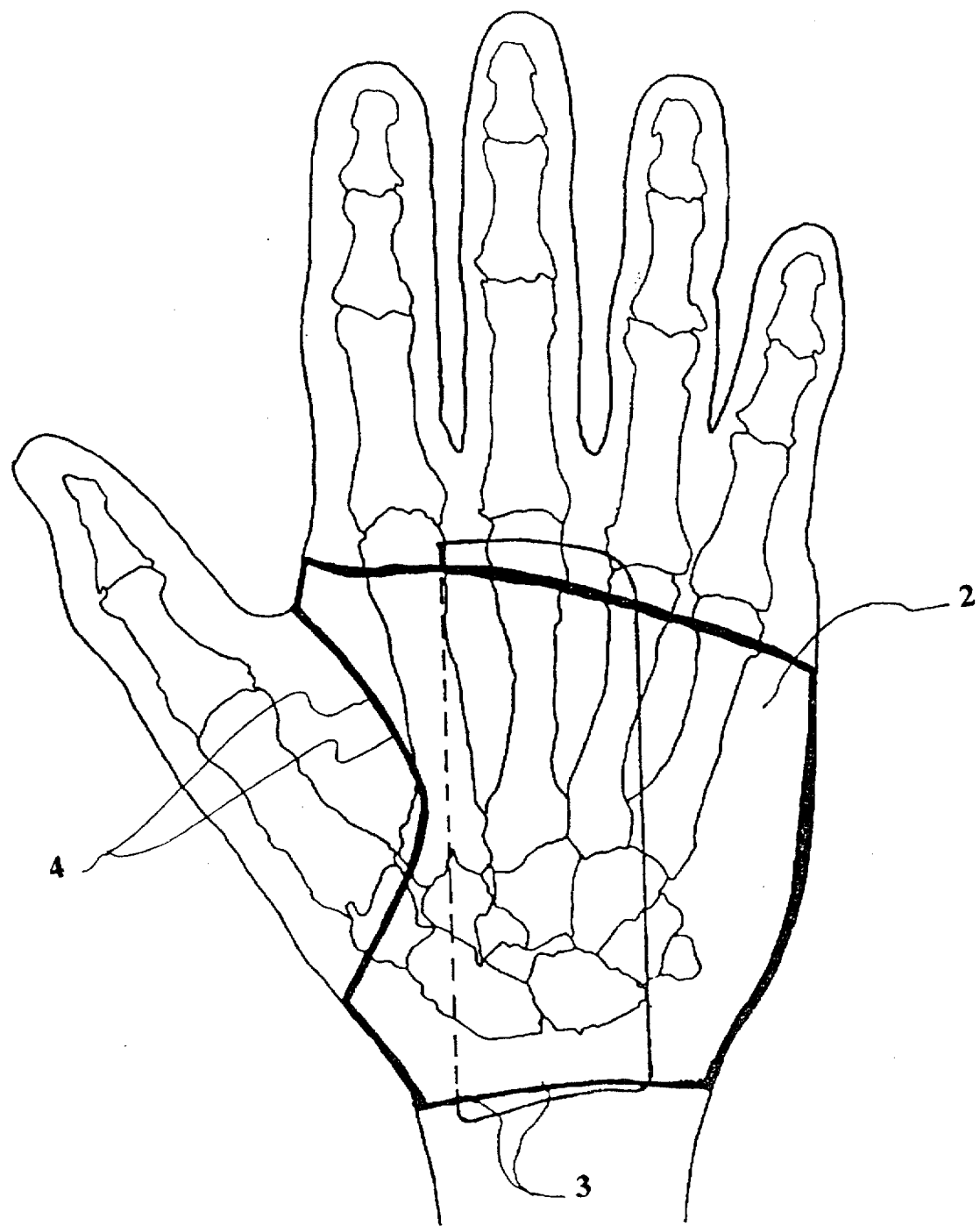
FIG. 5 is a back view of the orthosis worn on the hand.

Referring to FIGS. 1 to 5, where like numbers in the figures indicate like elements, this invention consists of a hand's intrapalmar orthosis (FIG. 1), which comprehends a semiflexible support (1), to be placed in the hand's palmar region, having a carpus area (5) and a metacarpus tongue (6). This semi flexible support (1) is made from plastic material in plate or sheet from, such as polypropylene, polyethylene or other material of similar characteristics. The semiflexible support (1) follows the hand's palmer contour, having a longitudinal arch (8) of front concavity, a transverse arch (9) of front concavity, a palmar center button (10) and a fastening gauntlet (2) to be incorporated to the hand (FIGS. 4,5). The gauntlet (2) covers the whole dorsal and palmar region of the hand, not including the fingers, with the exception of the thumb for which it has the thumb hole (4), closing in the back by means of VELCRO or the like (3). The gauntlet (2) doesn't extend past the close fold of the wrist nor does the distal extreme (7) of the gauntlet (2) extend past the palmar fold, nor reach the fingers.

Intrapalmar orthosis design (FIG. 1), when worn (FIGS. 4,5), provides an effective support to the hand's palmar zone, due to the semiflexible support (1), which performs a firm pressure upon the hand's carpus bones. The metacarpus tongue (6) design, allows the movement of the hand's external metacarpus, thus keeping the finger movements is free. Longitudinal (8) and transverse (9) arches of the semiflexible support (1) follow the hand's contour and give support to the carpus in the principal force lines crossing it, according to its normal biomechanism. The palmar center button (10) gives support to the hand's mechanic center, giving at the same time a support point to the orthosis.

The semiflexible support (1) stands in its place because it is included in the gauntlet (2) by means of a seam or other useful mean.

The intrapalmar orthosis (FIG. 1) is designed to perform its mechanical function only when the hand exerts a force in its normal functions, that is to say, during cylindrical, spherical, pincers' pressing, as well as in flat pressing (resting the hand in a flat surface). The intrapalmar orthosis (FIG. 1) has no mechanic effect during rest, thus being comfortable and well tolerated when used during long periods.

The gauntlet can be made of leather, fabric, woven elastic material, semielastic or non-elastic.

To attach the intrapalmar orthosis, (FIG. 1) having the structure of the invention previously mentioned on the user's hand, as shown in FIGS. 4 and 5, the thumb hole (4) is applied to the thumb, verifying that the semiflexible support (1) remains well secured to the hand's palmar region and closing the back extremes of the gauntlet (2), making sure they remain well adjusted in its joining seam (3).

This intrapalmar orthosis design can be made in different shapes than the one here disclosed, to treat particular cases, the semiflexible support (1) could have special support or pressure zones for one or many carpus bones requiring it. Thus, the basic form can be modified with the purpose of including metacarpus bones, as required.

Figure 1:
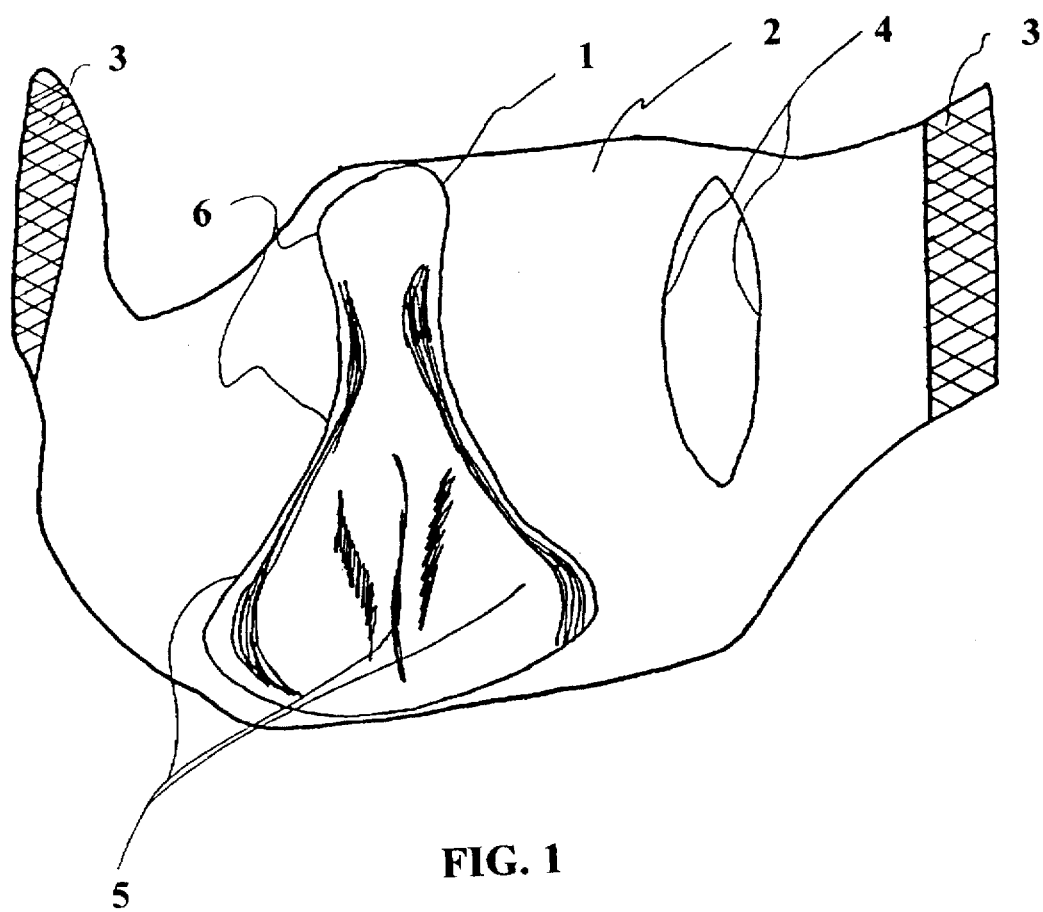
FIG. 1 is a perspective frontal view of the intrapalmar orthosis.
Figure 2:
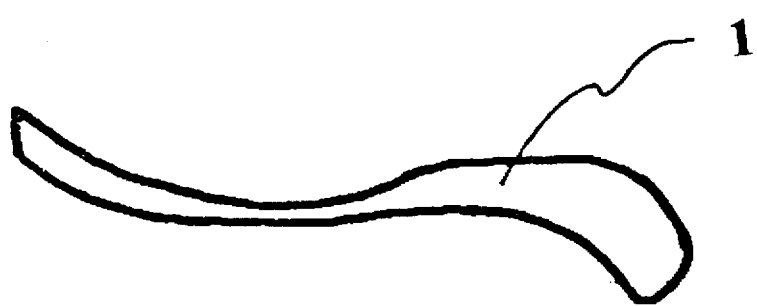
FIG. 2 is a lateral perspective view of the semiflexible support.
Figure 3:
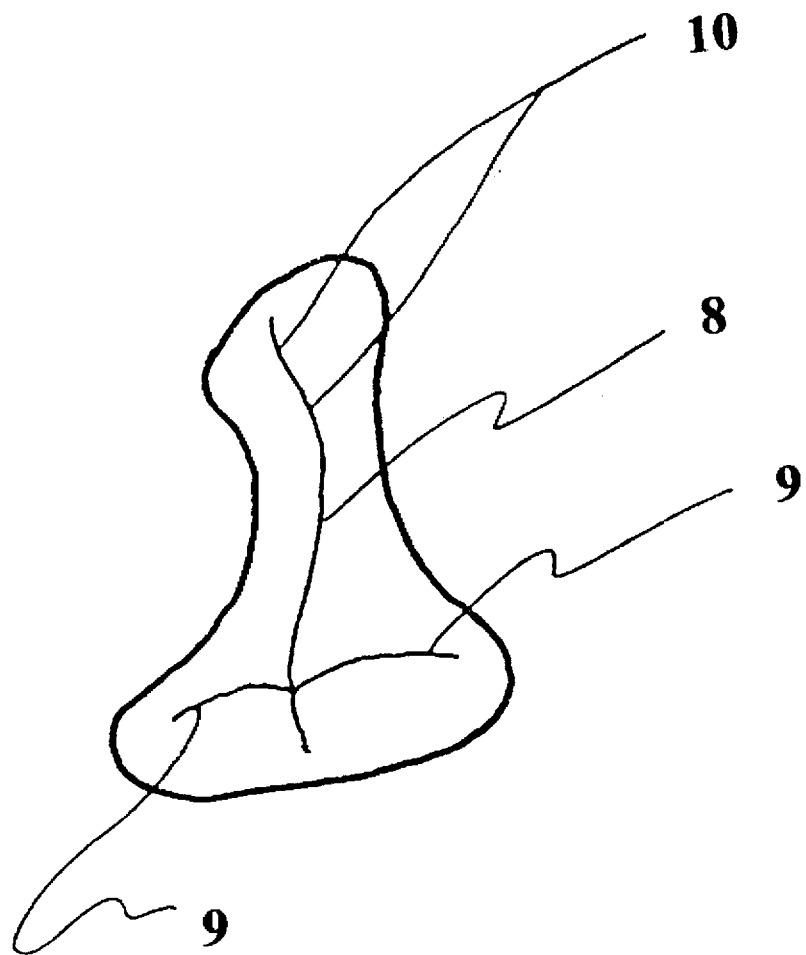
FIG. 3 is a perspective frontal view of the semiflexible support.

Electric or electronic elements with different purposes may be added to this intrapalmar splint (FIG. 1).

What is claimed is:

1. An intrapalmar orthosis to protect and give palmar region stability and support to the osseus carpus region of a hand without limiting normal movement of fingers and thumb of the hand or normal wrist movement during manual work, comprising in combination:

a flexible gauntlet shaped and sized to fit only around the palmar region of the hand terminating short of the fingers and wrist and apertured for slipping over the thumb, thereby to permit unimpeded movement of the fingers and wrist, and a semi-flexible palmar splint adapted to fit only over the carpus palmar region retained in said gauntlet and shaped with a carpus region from which extends a metacarpus tongue for following, covering and supporting dorsal and palmar contours of the hand in a rest position of the hand and to provide firm pressure on the palmar face of the carpus when the hand is doing manual work, said metacarpus tongue leaving fingers free to move and having a palmer center structure serving as a support center on the orthosis at a mechanic center of the hand, whereby protection and support is given to reduce instability of the osseous carpus and to reduce pain induced from said instability while doing manual work while introducing little interference with normal functions of the hand.

2. The orthesis of claim 1 wherein a splint contact surface follows the contour of the palm and the gauntlet and splint are cooperatively configured to avoid pressure on the hand at rest and to exert a force on the carpus bones when the hand is working.

3. The orthosis of claim 1 wherein the splint is configured with a carpus support area from which a metacarpus support tongue extends.

4. The orthosis of claim 3 wherein the carpus support area comprises a transverse arch surface configuration and the tongue comprises a longitudinal arch surface configuration.

* * * * *